United States Patent
Kadowaki et al.

(10) Patent No.: US 7,851,478 B2
(45) Date of Patent: Dec. 14, 2010

(54) AGENT FOR PREVENTING AND/OR TREATING MOVEMENT DISORDER

(75) Inventors: Takako Kadowaki, Shizuoka (JP); Minoru Kobayashi, Shizuoka (JP); Shizuo Shiozaki, Shizuoka (JP); Naoki Seno, Ibaraki (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 172 days.

(21) Appl. No.: 11/916,783

(22) PCT Filed: Jun. 7, 2006

(86) PCT No.: PCT/JP2006/311430

§ 371 (c)(1), (2), (4) Date: Jan. 25, 2008

(87) PCT Pub. No.: WO2006/132275

PCT Pub. Date: Dec. 14, 2006

(65) Prior Publication Data

US 2009/0105277 A1    Apr. 23, 2009

(30) Foreign Application Priority Data

Jun. 7, 2005 (JP) .............................. 2005-166981

(51) Int. Cl.
*A61K 31/505* (2006.01)
*C07D 491/00* (2006.01)

(52) U.S. Cl. ...................... 514/267; 544/251

(58) Field of Classification Search .......... 514/267; 544/251

See application file for complete search history.

(56) References Cited

U.S. PATENT DOCUMENTS

| | | | |
|---|---|---|---|
| 6,066,642 A | 5/2000 | Jacobson et al. | |
| 6,222,035 B1 | 4/2001 | Tsumuki et al. | |
| 6,545,000 B1 | 4/2003 | Shimada et al. | |
| 7,465,740 B2 * | 12/2008 | Neustadt et al. | 514/267 |
| 2002/0099061 A1 | 7/2002 | Neustadt et al. | |
| 2003/0171381 A1 | 9/2003 | Tulshian et al. | |
| 2003/0191130 A1 | 10/2003 | Neustadt et al. | |
| 2003/0212059 A1 * | 11/2003 | Boyle et al. | 514/217.06 |
| 2004/0097526 A1 | 5/2004 | Gillespie et al. | |
| 2004/0138235 A1 | 7/2004 | Grzelak et al. | |
| 2004/0152659 A1 | 8/2004 | Matsuoka et al. | |
| 2004/0198753 A1 | 10/2004 | Kase et al. | |
| 2005/0014815 A1 | 1/2005 | Sundermann et al. | |
| 2005/0090492 A1 | 4/2005 | Kuo et al. | |

FOREIGN PATENT DOCUMENTS

| | | |
|---|---|---|
| JP | 2000-516910 A | 12/2000 |
| JP | 2001-302648 A | 10/2001 |
| JP | 2003-535094 A | 11/2003 |
| JP | 2004-517862 A | 6/2004 |
| JP | 2005-506352 A | 3/2005 |
| JP | 2005-511697 A | 4/2005 |
| WO | WO 98/42711 A1 | 10/1998 |
| WO | WO 99/43678 A1 | 9/1999 |
| WO | WO 00/17201 A1 | 3/2000 |
| WO | WO 00/69464 A1 | 11/2000 |
| WO | WO 03/032996 * | 4/2003 |
| WO | WO 03/048156 A1 | 6/2003 |
| WO | WO 03/063876 A2 | 8/2003 |
| WO | WO 2004/092173 A2 | 10/2004 |
| WO | WO 2004/094431 A2 | 11/2004 |
| WO | WO 2005/044819 A1 | 5/2005 |
| WO | WO 2005/054245 A2 | 6/2005 |

OTHER PUBLICATIONS

Kim, et al., J. Med. Chem., 39: 4142-4148, 4143 (1996).*
Kim et al., *J. Med. Chem.*, 39: 4142-4148 (1996).
Brown et al., *IDrugs*, 5(5): 454-468 (Jan. 1, 2002).
Simola et al., *Experimental Neurology*, 189(1): 182-188 (Sep. 1, 2004).

* cited by examiner

*Primary Examiner*—James O Wilson
*Assistant Examiner*—Erich A Leeser
(74) *Attorney, Agent, or Firm*—Leydig, Voit & Mayer, Ltd.

(57) ABSTRACT

For example, an agent for preventing and/or treating movement disorder comprising, as an active ingredient, a triazolopyrimidine derivative having an adenosine $A_{2A}$ receptor antagonistic action, which is represented by the following formula (I):

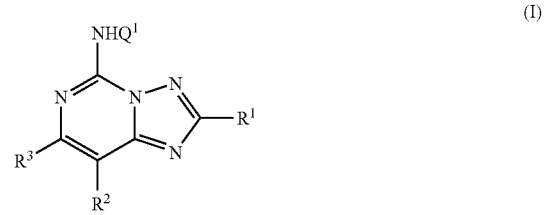

(wherein $R^1$ represents substituted or unsubstituted aryl or a substituted or unsubstituted heterocyclic group, $R^2$ represents a hydrogen atom, or the like, $R^3$ represents —$WR^4$, or the like, and $Q^1$ represents a hydrogen atom or 3,4-dimethoxybenzyl), or a pharmaceutically acceptable salt thereof, and the like are provided.

5 Claims, No Drawings

AGENT FOR PREVENTING AND/OR TREATING MOVEMENT DISORDER

TECHNICAL FIELD

The present invention relates to an agent for preventing and/or treating movement disorder.

BACKGROUND ART

Movement disorders are neurological disorders characterized by lack, decrease or incoordination of movement, or involuntary movements (for example, tremor, dyskinesia, chorea, ballism, dystonia, ataxia, akathisia, athetosis, tic, myoclonus etc.). Representative diseases with movement disorder include Parkinson's disease, Huntington's disease, essential tremor, tardive dyskinesia, restless legs syndrome, Tourette syndrome, progressive supranuclear palsy, spasmodic torticollis, or the like (THE MERCK INDEX 17th ed., Chapter 14; Nihon Rinsho, 1993, vol. 51, p. 2816-2822).

The neuronal assemblies responsible for the control of movement consists of the corticospinal tract that connects the cerebral cortex with the brain stem and the lower motor center of the spinal cord via medullary pyramid, the basal ganglia that directs output toward the cerebral cortex and the cerebellum which is the center of the movement-coordination. When one or more of these constituent elements are disordered, an abnormal movement pattern (movement disorder) appears. The etiology of movement disorder involves not only a neurodegenerative disease, but also a psychiatric disease, a drug effect, a mental process, or the like, where the detail of the disorder varies widely. According to the International Classification of Diseases, 10th edition (ICD-10) of WHO, the movement disorder is ranked as an "extrapyramidal disorder and abnormal behavior" or a "behavioral and emotional disorder generally developed in the infancy (childhood) and adolescence", including a wide range of from drug-induced type and psychogenic type to those caused by neurodegeneration of the basal ganglia.

Parkinson's disease, which is a representative disease associated with movement disorder, is a neurodegenerative disease that gradually advances with age. Its characteristic symptoms are, for example, resting tremor, rigidity, akinesia, abnormal postural reflex, or the like, which are called the four major symptoms of Parkinson's disease. Pathologically, denaturation or loss of dopaminergic neuron that projects from the substantia nigra, which is a part of the extrapyramidal system, to the corpus striatum, as well as appearance of Lewy body are observed, and a remarkable decrease in the corpus striatum dopamine content is seen. The prevalence is assumed to be 100-150 people in Japan, and 100-200 people in Europe and US, per 100,000 people, the age of onset is 50-65 years old in many cases, and the incidence increases as the age grows (Nihon Rinsho, 2004, vol. 62, p. 1603-1607; Nihon Rinsho, 1997, vol. 55, p. 9-15). In addition, the disease group with the development of some of the extrapyramidal symptoms as seen in Parkinson's disease is called parkinsonism (Parkinson's syndrome), which may be caused secondarily by, for example, cerebrovascular disorder, pharmaceutical agent, poisoning, tumor, trauma, or the like, or may be caused by various neurodegenerative diseases other than Parkinson's disease. As the pharmaceutical agent that can cause parkinsonism, for example, benzamide derivatives having a dopamine receptor blocking action (for example, antipsychotic agent, antidepressant, gastrointestinal prokinetic agent etc.), antipsychotic agents of phenothiazine series and butyrophenone series, calcium antagonist, antiarrhythmic, dopamine depleting agent, or the like can be mentioned (Naika, 2004, vol. 93, p. 648-652).

The basic treatment of Parkinson's disease is an L-DOPA replacement therapy supplementing the deficient dopamine, and dopamine agonist, MAO-B (monoamine oxidation enzyme B) inhibitor, COMT (catechol-O-methyltransferase) inhibitor, anticholinergic agent, amantadine, or the like are often used in combination (Rinsho Shinkeigaku, 2002, vol. 42, p. 421-494). However, a long-term administration of L-DOPA in the L-DOPA replacement therapy (L-DOPA therapy) causes the problematic development of motor complications such as involuntary movement (e.g., dyskinesia, dystonia, or the like), wearing-off phenomenon, on-off fluctuation, or the like (THE MERCK INDEX 17th ed., Chapter 14; Nihon Rinsho, 2004, vol. 62, p. 1594-1749). Generally, once a motor complication is developed, it cannot be treated with L-DOPA or other dopamine agonist. Dyskinesia mainly includes choreiform movements, which may systemically or partially occur from the face such as in the mouth, jaw, tongue, or the like to the extremities. Dystonia frequently occurs on awakening, with equinovarus accompanying bending of the toe, and frequently with a pain. While the etiology thereof has not been elucidated sufficiently, the inability to maintain L-DOPA concentration at a certain level with the progression of dopamine neurodegeneration is considered to contribute to the motor complications (Nihon Rinsho, 2004, vol. 62, p. 1711-1715). To deal with dyskinesia, the dose of L-DOPA needs to be reduced and, when the reduction is ineffective, amantadine is added. On the other hand, for dystonia, more dopamine agonist, L-DOPA, MAO-B inhibitor and the like are added. Since these symptoms frequently appear in the advanced stage, reduction of the dose of pharmaceutical agent often aggravates the symptoms of Parkinson's disease to the extent that the activity of daily living (ADL) is affected (Rinsho Shinkeigaku, 2002, vol. 42, p. 421-494; Nihon Rinsho, 2004, vol. 62, p. 1711-1715). Moreover, side effects of nausea, vomiting, orthostatic hypotension, psychiatric symptom, or the like due to dopamine receptor stimulation by the administration of a dopaminergic pharmaceutical agent such as L-DOPA is also problematic, and a new treatment method replacing the dopaminergic pharmaceutical agents is expected.

As the triazolopyrimidine derivative having an adenosine $A_{2A}$ receptor antagonistic action, for example, many compounds such as [1,2,4]triazolo[1,5-c]pyrimidine derivative, [1,2,4]triazolo[1,5-a]pyrimidine derivative are known (see, for example, patent reference 1, patent reference 2, patent reference 3, patent reference 4, patent reference 5, patent reference 6, patent reference 7, patent reference 8 etc.). Moreover, it is known that a compound having an adenosine $A_{2A}$ receptor antagonistic action is effective for the treatment of extrapyramidal disorder, dystonia, restless legs syndrome, or the like (see patent reference 9).

patent reference 1: WO98/42711 patent reference 2: WO00/17201 patent reference 3: WO99/43678 patent reference 4: WO01/92264 patent reference 5: WO00/69464 patent reference 6: WO03/48156 patent reference 7: WO03/32996 patent reference 8: WO03/48163 patent reference 9: US Publication No. 2004/0138235

DISCLOSURE OF THE INVENTION

Problems to be Solved by the Invention

An object of the present invention is to provide an agent for preventing and/or treating movement disorder, comprising, for example, a triazolopyrimidine derivative having an adenosine $A_{2A}$ receptor antagonistic action or a pharmaceutically acceptable salt thereof as an active ingredient, and the like.

Means of Solving the Problems

The present invention relates to the following (1)-(28).

(1) An agent for preventing and/or treating involuntary movement, comprising, as an active ingredient, a triazolopyrimidine derivative having an adenosine $A_{2A}$ receptor antagonistic action or a pharmaceutically acceptable salt thereof.

(2) The agent for preventing and/or treating involuntary movement according to the above-mentioned (1), wherein the triazolopyrimidine derivative having an adenosine $A_{2A}$ receptor antagonistic action is a compound represented by the formula (I):

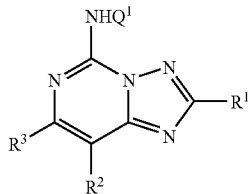

(I)

[wherein $R^1$ represents substituted or unsubstituted aryl or a substituted or unsubstituted heterocyclic group, $R^2$ represents a hydrogen atom, halogen, substituted or unsubstituted lower alkyl, substituted or unsubstituted aryl or a substituted or unsubstituted heterocyclic group, $R^3$ represents a hydrogen atom, halogen or —$WR^4$— (wherein W is —O— or —S—, $R^4$ represents substituted or unsubstituted lower alkyl, substituted or unsubstituted aryl or a substituted or unsubstituted heterocyclic group), and $Q^1$ represents a hydrogen atom or 3,4-dimethoxybenzyl].

(3) The agent for preventing and/or treating involuntary movement according to the above-mentioned (1), wherein the triazolopyrimidine derivative having an adenosine $A_{2A}$ receptor antagonistic action is a compound represented by the formula (II):

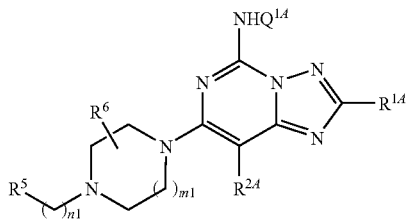

(II)

[wherein $R^{1A}$ represents substituted or unsubstituted aryl or a substituted or unsubstituted aromatic heterocyclic group, $R^{2A}$ represents a hydrogen atom, halogen, substituted or unsubstituted lower alkyl, substituted or unsubstituted aryl or substituted or unsubstituted aromatic heterocyclic group, n1 and m1 are the same or different and each represents an integer of 0-4, $Q^{1A}$ represents a hydrogen atom or 3,4-dimethoxybenzyl, $R^5$ represents a hydrogen atom, substituted or unsubstituted aryl, a substituted or unsubstituted heterocyclic group or —$CR^7R^8R^9$ (wherein $R^7$, $R^8$ and $R^9$ are the same or different and each represents a hydrogen atom, hydroxy, substituted or unsubstituted lower alkyl, substituted or unsubstituted lower alkoxy, substituted or unsubstituted aryl or a substituted or unsubstituted heterocyclic group, or $R^8$ and $R^9$ are combined together with the adjacent carbon atom thereto to form a substituted or unsubstituted carbocycle), and $R^6$ represents a hydrogen atom, halogen, hydroxy or substituted or unsubstituted lower alkyl].

(4) The agent for preventing and/or treating involuntary movement according to the above-mentioned (3), wherein $R^5$ is —$CR^{7A}R^{8A}R^{9A}$ (wherein $R^{7A}$ is hydroxy, hydroxy-lower alkyl, substituted or unsubstituted lower alkoxy or imidazo [1,2-a]pyridyl, and $R^{8A}$ and $R^{9A}$ are the same or different and each represents a hydrogen atom, substituted or unsubstituted lower alkyl or substituted or unsubstituted aryl, or $R^{8A}$ and $R^{9A}$ are combined together with the adjacent carbon atom thereto to form a substituted or unsubstituted carbocycle).

(5) The agent for preventing and/or treating involuntary movement according to the above-mentioned (1), wherein the triazolopyrimidine derivative having an adenosine $A_{2A}$ receptor antagonistic action is a compound represented by the formula (III):

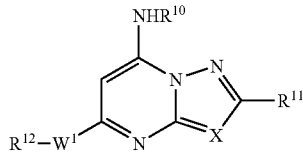

(III)

[wherein $R^{10}$ represents a hydrogen atom, substituted or unsubstituted lower alkyl or substituted or unsubstituted lower alkanoyl, $R^{11}$ represents a substituted or unsubstituted heterocyclic group, $R^{12}$ represents a hydrogen atom, substituted or unsubstituted lower alkyl, substituted or unsubstituted lower alkenyl, substituted or unsubstituted cycloalkyl, substituted or unsubstituted aryl or a substituted or unsubstituted heterocyclic group, $W^1$ represents a single bond, —O—, —S—, —S(=O)—, —S(=O)$_2$— or —$NR^{13}$— (wherein $R^{13}$ is a hydrogen atom or substituted or unsubstituted lower alkyl), and X represents =N— or —$CR^{14}$— (wherein $R^{14}$ is a hydrogen atom or substituted or unsubstituted lower alkyl)].

(6) The agent for preventing and/or treating involuntary movement according to the above-mentioned (1), wherein the triazolopyrimidine derivative having an adenosine $A_{2A}$ receptor antagonistic action is a compound represented by the formula (IV):

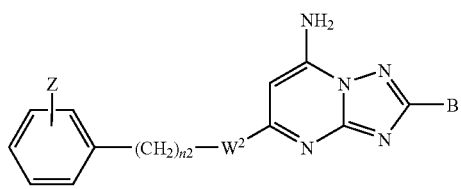

(IV)

(wherein

B represents furyl or thienyl, $W^2$ represents a single bond, —O— or —S—,

Z represents a hydrogen atom, halogen or substituted or unsubstituted lower alkyl, and n2 represents an integer of 0-5).

(7) The agent for preventing and/or treating involuntary movement according to the above-mentioned (1), wherein the triazolopyrimidine derivative having an adenosine $A_{2A}$ receptor antagonistic action is a compound represented by the formula (V):

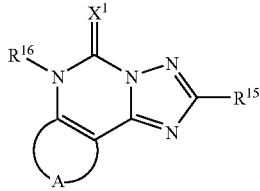

(V)

[wherein $R^{15}$ represents substituted or unsubstituted aryl or a substituted or unsubstituted heterocyclic group, $R^{16}$ represents a hydrogen atom, substituted or unsubstituted lower alkyl, substituted or unsubstituted lower alkenyl, substituted or unsubstituted lower alkynyl, substituted or unsubstituted cycloalkyl, substituted or unsubstituted aryl or a substituted or unsubstituted heterocyclic group, $X^1$ represents an oxygen atom, a sulfur atom or $NR^{17}$ (wherein $R^{17}$ represents a hydrogen atom, substituted or unsubstituted lower alkyl, substituted or unsubstituted cycloalkyl or substituted or unsubstituted aryl), and A is combined together with the adjacent two carbon atoms thereto to form a substituted or unsubstituted carbocycle or a substituted or unsubstituted heterocycle].

(8) The agent for preventing and/or treating involuntary movement according to the above-mentioned (1), wherein the triazolopyrimidine derivative having an adenosine $A_{2A}$ receptor antagonistic action is a compound represented by the formula (VI):

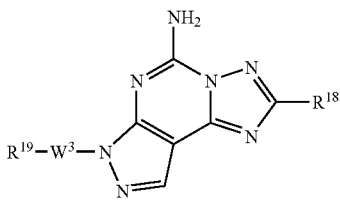

(VI)

[wherein $R^{18}$ represents substituted or unsubstituted cycloalkenyl, substituted or unsubstituted aryl or a substituted or unsubstituted aromatic heterocyclic group, $R^{19}$ represents substituted or unsubstituted lower alkyl, and $W^3$ represents a single bond or —C(=O)—].

(9) The agent for preventing and/or treating involuntary movement according to the above-mentioned (1), wherein the triazolopyrimidine derivative having an adenosine $A_{2A}$ receptor antagonistic action is a compound represented by the formula (VI-A):

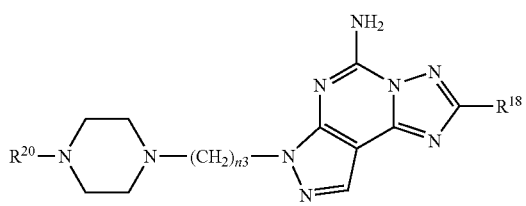

(VI-A)

(wherein $R^{18}$ is as defined above, n3 represents an integer of 1-4, and $R^{20}$ represents substituted or unsubstituted aryl or a substituted or unsubstituted heterocyclic group;

for example, 5-amino-2-(2-furyl)-7-(2-{4-[4-(2-methoxyethoxy)phenyl]piperazinyl}ethyl)pyrazolo[4,3-e]-1,2,4-triazolo[1,5-c]pyrimidine, and the like).

(10) The agent for preventing and/or treating involuntary movement according to the above-mentioned (1), wherein the triazolopyrimidine derivative having an adenosine $A_{2A}$ receptor antagonistic action is a compound represented by the formula (VII):

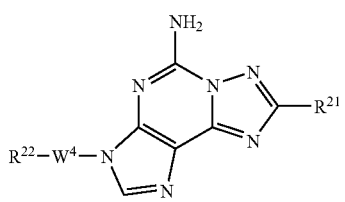

(VII)

(wherein $R^{21}$ represents substituted or unsubstituted aryl, substituted or unsubstituted cycloalkenyl or a substituted or unsubstituted heterocyclic group, $W^4$ represents a single bond or —C(=O)—, and $R^{22}$ represents substituted or unsubstituted lower alkyl).

(11) The agent for preventing and/or treating involuntary movement according to the above-mentioned (1), wherein the triazolopyrimidine derivative having an adenosine $A_{2A}$ receptor antagonistic action is a compound represented by the formula (VII-A):

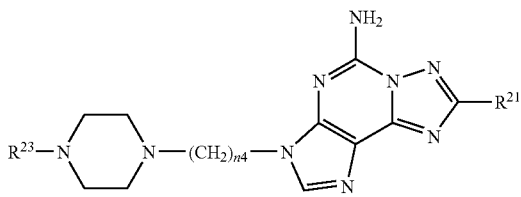

(wherein $R^{21}$ is as defined above, n4 is an integer of 1-4, and $R^{23}$ is substituted or unsubstituted aryl or a substituted or unsubstituted heterocyclic group;

for example, 5-amino-2-(2-furyl)-7-(2-{4-[4-(2-methoxyethoxy)phenyl]piperazinyl}ethyl)pyrazolo[4,5-e]-1,2,4-triazolo[1,5-c]pyrimidine, and the like).

(12) The agent for preventing and/or treating involuntary movement according to any of the above-mentioned (1) to (11), wherein the involuntary movement is a motor complication in the treatment of Parkinson's disease.

(13) The agent for preventing and/or treating involuntary movement according to any of the above-mentioned (1) to (11), wherein the involuntary movement is dyskinesia in the treatment of Parkinson's disease.

(14) The agent for preventing and/or treating involuntary movement according to any of the above-mentioned (1) to (11), wherein the involuntary movement is dyskinesia in the treatment of Parkinson's disease with L-DOPA and/or a dopamine agonist.

(15) The agent for preventing and/or treating involuntary movement according to any of the above-mentioned (1) to (11), wherein the involuntary movement is selected from the group consisting of tremor, dyskinesia, chorea, ballism, dystonia, ataxia, akathisia, athetosis, tic and myoclonus.

(16) The agent for preventing and/or treating involuntary movement according to any of the above-mentioned (1) to (11), wherein the involuntary movement is selected from the group consisting of dyskinesia, tardive dyskinesia, chorea, ballism, dystonia, tardive dystonia, ataxia, akathisia, athetosis, tic and myoclonus.

(17) The agent for preventing and/or treating involuntary movement according to any of the above-mentioned (1) to (11), wherein the involuntary movement is selected from the group consisting of dyskinesia and tardive dyskinesia.

(18) A pharmaceutical agent for reducing the dose of L-DOPA in the treatment of Parkinson's disease with L-DOPA and/or a dopamine agonist, which comprises, as an active ingredient, the triazolopyrimidine derivative having an adenosine $A_{2A}$ receptor antagonistic action or the pharmaceutically acceptable salt thereof described in any of the above-mentioned (1) to (11).

(19) An agent for preventing and/or treating movement disorder, which comprises, as an active ingredient, the triazolopyrimidine derivative having an adenosine $A_{2A}$ receptor antagonistic action or the pharmaceutically acceptable salt thereof described in any of the above-mentioned (1) to (11).

(20) An agent for preventing and/or treating movement disorder characterized by involuntary movement, which comprises, as an active ingredient, the triazolopyrimidine derivative having an adenosine $A_{2A}$ receptor antagonistic action or the pharmaceutically acceptable salt thereof described in any of the above-mentioned (1) to (11).

(21) Use of a triazolopyrimidine derivative having an adenosine $A_{2A}$ receptor antagonistic action or a pharmaceutically acceptable salt thereof for the production of an agent for preventing and/or treating involuntary movement.

(22) Use of a triazolopyrimidine derivative having an adenosine $A_{2A}$ receptor antagonistic action or a pharmaceutically acceptable salt thereof for the production of an agent for reducing the dose of L-DOPA in the treatment of Parkinson's disease with L-DOPA and/or a dopamine agonist.

(23) Use of a triazolopyrimidine derivative having an adenosine $A_{2A}$ receptor antagonistic action or a pharmaceutically acceptable salt thereof for the production of an agent for preventing and/or treating movement disorder.

(24) Use of a triazolopyrimidine derivative having an adenosine $A_{2A}$ receptor antagonistic action or a pharmaceutically acceptable salt thereof for the production of an agent for preventing and/or treating movement disorder characterized by involuntary movement.

(25) A method of preventing and/or treating involuntary movement, which comprises administering an effective amount of a triazolopyrimidine derivative having an adenosine $A_{2A}$ receptor antagonistic action or a pharmaceutically acceptable salt thereof to a patient in need thereof.

(26) A method of reducing the dose of L-DOPA in the treatment of Parkinson's disease with L-DOPA and/or a dopamine agonist, which comprises administering an effective amount of a triazolopyrimidine derivative having an adenosine $A_{2A}$ receptor antagonistic action or a pharmaceutically acceptable salt thereof to a patient in need thereof.

(27) A method of preventing and/or treating movement disorder, which comprises administering an effective amount of a triazolopyrimidine derivative having an adenosine $A_{2A}$ receptor antagonistic action or a pharmaceutically acceptable salt thereof to a patient in need thereof.

(28) A method of preventing and/or treating movement disorder characterized by involuntary movement, which comprises administering an effective amount of a triazolopyrimidine derivative having an adenosine $A_{2A}$ receptor antagonistic action or a pharmaceutically acceptable salt thereof to a patient in need thereof.

Effect of the Invention

The present invention provides, for example, an agent for preventing and/or treating movement disorder, which comprises, as an active ingredient, a triazolopyrimidine derivative having an adenosine $A_{2A}$ receptor antagonistic action or a pharmaceutically acceptable salt thereof, and the like.

BEST MODE FOR CARRYING OUT THE INVENTION

Examples of the movement disorder to be prevented and/or treated in the present invention include a disorder characterized by lack, decrease or incoordination of movement, involuntary movement (for example, tremor, dyskinesia, chorea, ballism, dystonia, ataxia, athetosis, akathisia, tic, myoclonus etc.) and a combination of these symptoms, or the like. Of these, a movement disorder characterized by an involuntary movement is favorably prevented and/or treated. In addition to the above-mentioned disorders, for example, movement disorders characterized by an involuntary movement such as motor complications (for example, dyskinesia, on-off fluctuation, wearing-off phenomenon etc.) in the treatment of Parkinson's disease (for example, the treatment of Parkinson's disease with L-DOPA and/or a dopamine agonist etc.), or the like are also favorably prevented and/or treated.

Moreover, examples of the involuntary movement to be prevented and/or treated in the present invention include those mentioned above, or the like. Of those, tremor, dyskinesia, chorea, ballism, akathisia, tic, myoclonus, or the like are favorably prevented and/or treated.

Examples of the disease with the above-mentioned movement disorder include Huntington's disease, essential tremor, tardive dyskinesia, tardive dystonia, Tourette syndrome, progressive supranuclear palsy, spasmodic torticollis, or the like.

As for a triazolopyrimidine derivative having an adenosine $A_{2A}$ receptor antagonistic action, a triazolopyrimidine derivative having an action to inhibit, suppress or cease at least one of the physiological actions involving adenosine, or the like, by preventing or prophylactically inhibiting the binding to an adenosine $A_{2A}$ receptor or binding of adenosine to an adenosine $A_{2A}$ receptor can be recited. For example, triazolopyrimidine derivatives described in WO98/42711, WO00/17201, WO99/43678, WO01/92264, WO00/69464, WO03/48156, WO03/32996, WO03/48163, and the like can be recited. Specifically, for example, compounds represented by the above-mentioned formulas (I)-(VII), (VI-A) and (VII-A) (hereinafter to be referred to as compounds (I)-(VII), (VI-A) and (VII-A), respectively), and the like can be recited. Of these, compound (I), (II), (VI) or (VI-A), and the like are preferable, and compound (II) or (VI-A), and the like are particularly preferable.

In the definitions of each group in the formulas (I)-(VII), (VI-A) and (VII-A), examples of the lower alkyl moiety of the lower alkyl, hydroxy lower alkyl, lower alkoxy and lower alkanoyl include straight chain or branched alkyl having 1 to 6 carbon atoms, and specifically include methyl, ethyl, propyl, isopropyl, butyl, isobutyl, sec-butyl, tert-butyl, pentyl, neopentyl, hexyl, and the like.

Examples of the lower alkenyl include straight chain or branched alkenyl having 2 to 6 carbon atoms, and specifically include vinyl, allyl, methacryl, crotyl, 3-butenyl, 2-pentenyl, 4-pentenyl, 2-hexenyl, 5-hexenyl, and the like.

Examples of the lower alkynyl include straight chain or branched alkynyl having 2 to 6 carbon atoms, and specifically include ethynyl, propargyl, 2-butynyl, 3-butynyl, 2-pentynyl, 4-pentynyl, 2-hexynyl, 5-hexynyl, 4-methyl-2-pentynyl, and the like.

Examples of the cycloalkyl include cycloalkyl having 3 to 8 carbon atoms, and specifically include cyclopropyl, cyclobutyl, cyclopentyl, cyclohexyl, cycloheptyl, cyclooctyl, and the like.

Examples of the cycloalkenyl include cycloalkenyl having 4 to 8 carbon atoms, and specifically include cyclobutenyl, cyclopentenyl, cyclohexenyl, cycloheptenyl, cyclooctenyl, and the like.

Halogen means each atom of fluorine, chlorine, bromine and iodine.

Examples of the aryl include aryl having 6 to 14 carbon atoms, and specifically include phenyl, naphthyl, anthryl, and the like.

Examples of the aromatic heterocyclic group include a 5-membered or 6-membered monocyclic aromatic heterocyclic group containing at least one atom selected from nitrogen atom, oxygen atom and sulfur atom, a bicyclic or tricyclic fused-ring aromatic heterocyclic group containing at least one atom selected from nitrogen atom, oxygen atom and sulfur atom, in which 3- to 8-membered ring(s) is/are fused, and the like, and specifically include pyridyl, pyrazinyl, pyrimidinyl, pyridazinyl, oxopyridazinyl, quinolyl, isoquinolyl, phthalazinyl, quinazolinyl, quinoxalinyl, naphthyridinyl, cinnolinyl, pyrrolyl, pyrazolyl, imidazolyl, triazinyl, triazolyl, tetrazolyl, thienyl, furyl, thiazolyl, isothiazolyl, oxazolyl, isoxazolyl, oxadiazolyl, thiadiazolyl, oxooxadiazolyl, indolyl, isoindolyl, indazolyl, 2-oxobenzoimidazolyl, benzofuryl, benzothienyl, benzoimidazolyl, benzotriazolyl, benzothiazolyl, benzoxazolyl, purinyl, dibenzofuranyl, imidazo[1,2-a]pyridyl, and the like.

Examples of the heterocyclic group include an alicyclic heterocyclic group in addition to the groups recited in the definition of the aforementioned aromatic heterocyclic group. Examples of the alicyclic heterocyclic group include a 5-membered or 6-membered monocyclic alicyclic heterocyclic group containing at least one atom selected from nitrogen atom, oxygen atom and sulfur atom, a bicyclic or tricyclic fused-ring alicyclic heterocyclic group containing at least one atom selected from nitrogen atom, oxygen atom and sulfur atom, in which 3- to 8-membered ring(s) is/are fused, and the like, and specifically include pyranyl, thiopyranyl, pyrrolidinyl, piperidino, piperidinyl, piperazinyl, imidazolidinyl, thiazolidinyl, morpholino, morpholinyl, thiomorpholino, thiomorpholinyl, homopiperidino, homopiperazinyl, tetrahydropyridinyl, dihydroisoquinolyl, tetrahydroquinolyl, tetrahydroisoquinolyl, oxazolinyl, oxazolidinyl, oxooxazolidinyl, oxadiazolinyl, oxiranyl, tetrahydrofuranyl, tetrahydropyranyl, dihydrobenzofuranyl, oxopiperazinyl, 2-oxopyrrolidinyl, dioxolanyl, benzodioxolanyl, benzodioxinyl, benzodioxepinyl, benzopyranyl, benzodihydropyranyl, perhydrodiazepinyl, perhydrodiazocinyl, perhydrodiazoninyl, and the like.

Examples of the heterocycle formed together with the adjacent two carbon atoms include a 5-membered or 6-membered monocyclic heterocycle containing at least one atom selected from nitrogen atom, oxygen atom and sulfur atom, a bicyclic or tricyclic fused-ring heterocycle containing at least one atom selected from nitrogen atom, oxygen atom and sulfur atom, in which 3- to 8-membered ring(s) is/are fused, and the like, and specifically include pyrrole, pyran, thiopyran, pyridine, thiazole, imidazole, pyrimidine, triazine, indole, quinoline, benzothiazole, pyrroline, tetrahydropyridine, tetrahydropyrazine, tetrahydroquinoline, tetrahydroisoquinoline, and the like.

Examples of the carbocycle formed together with the adjacent two carbon atoms include cycloalkene having 4 to 8 carbon atoms, and the like, and specifically include cyclobutene, cyclopentene, cyclohexene, cycloheptene, cyclooctene, and the like.

Examples of the carbocycle formed together with the adjacent carbon atom include cycloalkane and cycloalkene, each having 4 to 8 carbon atoms, and the like, and specifically include cyclobutane, cyclopentane, cyclohexane, cycloheptane, cyclooctane, cyclobutene, cyclopentene, cyclohexene, cycloheptene, cyclooctene, and the like.

Examples of the substituent (A) for the substituted lower alkyl, substituted lower alkoxy, substituted lower alkanoyl, substituted lower alkenyl and substituted lower alkynyl include 1 to 3 substituents which may be the same or different, and which are specifically hydroxy, cyano, nitro, carboxy, carbamoyl, amino, benzyloxy, phenyloxy, halogen, substituted or unsubstituted lower alkoxy, cycloalkyl, lower alkanoyl, lower alkoxycarbonyl, lower alkylamino, di-lower alkylamino, substituted or unsubstituted aryl, substituted or unsubstituted heterocyclic group, or the like.

The halogen, cycloalkyl, aryl and heterocyclic group recited as examples of substituent (A) are each as defined above, and the lower alkyl moiety of lower alkoxy, lower alkanoyl, lower alkoxycarbonyl, lower alkylamino and di-lower alkylamino has the same definition as the aforementioned lower alkyl, and the two lower alkyl moieties of di-lower alkylamino may be the same or different.

Examples of the substituent of the substituted aryl and substituted heterocyclic group recited as examples of substituent (A) include the substituents to be recited later as examples of substituent (C), and the like. Examples of substituent (a) for the substituted lower alkoxy include 1 to 3 substituents which may be the same or different, and specifically are halogen, hydroxy, amino, carboxy, azido, lower alkoxy, lower alkoxycarbonyl, and the like. Halogen recited as examples of substituent (a) is as defined above, and the lower alkyl moiety of lower alkoxy and lower alkoxycarbonyl has the same definition as the aforementioned lower alkyl.

Examples of substituent (C) for the substituted cycloalkyl, substituted cycloalkenyl, substituted carbocycle formed together with the adjacent carbon atom, substituted carbocycle formed together with the adjacent two carbon atoms, substituted aryl, substituted heterocyclic group, substituted aromatic heterocyclic group and substituted heterocycle formed together with the adjacent two carbon atoms include 1 to 3 substituents which may be the same or different, and specifically are lower alkyl, lower alkenyl, lower alkynyl, hydroxy, substituted or unsubstituted lower alkoxy, halogen, nitro, amino, lower alkylamino, di-lower alkylamino, trifluoromethyl, trifluoromethoxy, aralkyl, aralkyloxy, aryl, aryloxy, lower alkanoyl, lower alkanoyloxy, aroyl, aroyloxy, arylalkanoyloxy, carboxy, lower alkoxycarbonyl, lower alkylcarbamoyl, di-lower alkylcarbamoyl, sulfo, lower alkoxysulfonyl, lower alkylsulfamoyl, di-lower alkylsulfamoyl, and the like.

The lower alkyl moiety of the lower alkyl, lower alkoxy, lower alkylamino, di-lower alkylamino, lower alkanoyl, lower alkanoyloxy, lower alkoxycarbonyl, lower alkylcarbamoyl, di-lower alkylcarbamoyl, lower alkoxysulfonyl, lower alkylsulfamoyl and di-lower alkylsulfamoyl recited as examples of substituent (C) has the same definition as the aforementioned lower alkyl, and halogen, lower alkenyl and lower alkynyl each are as defined above. The two lower alkyl moieties of di-lower alkylamino, di-lower alkylcarbamoyl and di-lower alkylsulfamoyl may be respectively the same or different. The aryl moiety of the aryl and aryloxy has the same definition as the aforementioned aryl, and examples of the aralkyl moiety of aralkyl and aralkyloxy include benzyl, phenethyl, or the like. Examples of the aroyl moiety of aroyl and aroyloxy include benzoyl, naphthoyl, and the like. Examples of the arylalkyl moiety of arylalkanoyloxy include benzyl, phenethyl, and the like.

Examples of substituent (c) of the substituted lower alkoxy recited as example of the substituent (C) include the substituents recited as examples of the aforementioned substituent (a), and the like.

Examples of the pharmaceutically acceptable salt of a triazolopyrimidine derivative having an adenosine $A_{2A}$ receptor antagonistic action include acid addition salt, metal salt, ammonium salt, organic amine addition salt, amino acid addition salt, and the like, which are pharmaceutically acceptable.

Examples of the pharmaceutically acceptable acid addition salt of a triazolopyrimidine derivative having an adenosine $A_{2A}$ receptor antagonistic action include inorganic acid salt such as hydrochloride, sulfate, or phosphate, organic acid salt such as acetate, maleate, fumarate, tartrate, citrate, or methanesulfonate, examples of the pharmaceutically acceptable metal salt include alkali metal salt such as sodium salt or potassium salt, alkaline earth metal salt such as magnesium salt, calcium salt, aluminum salt, or zinc salt, examples of the pharmaceutically acceptable ammonium salt include a salt of, for example, ammonium or tetramethylammonium, examples of the pharmaceutically acceptable organic amine addition salt include an addition salt of, for example, morpholine, piperidine, and the like, or examples of the pharmaceutically acceptable amino acid addition salt include an addition salt of, for example, lysin, glycine, phenylalanine, and the like.

Compounds (I)-(VII), (VI-A) and (VII-A) as well as pharmaceutically acceptable salts thereof can be respectively produced, for example, by the methods disclosed in WO98/42711, WO00/17201, WO99/43678, WO01/92264, WO00/69464, WO03/48156, WO03/32996, WO03/48163, or the like, or in a similar manner thereto. The object compound of each production method can be isolated and purified by a purification method conventionally used in organic synthetic chemistry, for example, by subjecting to filtration, extraction, washing, drying, concentration, recrystallization, various chromatographs, and the like.

When a salt of a triazolopyrimidine derivative having an adenosine $A_{2A}$ receptor antagonistic action such as compounds (I)-(VII), (VI-A), (VII-A), and the like is desired and when a triazolopyrimidine derivative having an adenosine $A_{2A}$ receptor antagonistic action such as compounds (I)-(VII), (VI-A), (VII-A), and the like is obtained in the form of a salt, the salt can be directly purified and, when it is obtained in a free form, a triazolopyrimidine derivative having an adenosine $A_{2A}$ receptor antagonistic action such as compounds (I)-(VII), (VI-A), (VII-A), and the like may be dissolved or suspended in a suitable solvent and an acid or base may be added to form a salt.

The triazolopyrimidine derivative having an adenosine $A_{2A}$ receptor antagonistic action such as compounds (I)-(VII), (VI-A), (VII-A), and the like, or pharmaceutically acceptable salts thereof may be present in the form of an adduct with water or various solvents. Such adducts can also be used as an agent for preventing and/or treating movement disorder, or the like of the present invention.

The triazolopyrimidine derivative having an adenosine $A_{2A}$ receptor antagonistic action such as compounds (I)-(VII), (VI-A), (VII-A), and the like may be present as a stereoisomer such as an optical isomer, and the like. All possible isomers including these isomers and mixtures of the isomers can be used in the present invention.

Specific examples of a triazolopyrimidine derivative having an adenosine $A_{2A}$ receptor antagonistic action are shown in Table 1.

TABLE 1

| Compound No. | |
|---|---|
| 1 | (structure: triazolopyrimidine with NH2, furan, piperazine, and H3C-C(OH)(CH3)-CH2- substituent) |
| 2 | (structure: pyrazolo-triazolopyrimidine with NH2, furan, piperazine, and 4-(2-methoxyethoxy)phenyl substituent) |

The effect of the present invention is specifically explained by referring to the following Test Examples.

Test Example 1

Antiparkinsonian Effect in the Parkinson's Disease Model Rats

6-OHDA treated rats (Parkinson's disease model rat) were prepared by destroying unilateral nigrostriatal dopamine neurons of the brain with 6-hydroxydopamine (referred to as 6-OHDA), which is a dopaminergic neurotoxin. This model is known to induce a rotational behavior (contralateral rotational behavior) in the direction opposite to the lesioned side by the administration of L-DOPA and/or dopamine agonist, and the contralateral rotational behavior is used as an index of the antiparkinsonian activity (Acta Psychiatrica Scandinavica Supplement, 1971, vol. 367, p. 69-93).

Test Method:

For the test, SD male rats (6-week-old, CHARLES RIVER LABORATORIES JAPAN, INC.) were used. Under pentobarbital anesthesia, the rats were fixed on a stereotaxic instrument (SR-6, NARISHIGE CO., LTD., Tokyo), and 6-OHDA (8 μg/2 μL; Sigma-Aldrich, St. Louis, Mo., USA) was injected into the left medial forebrain bundle (A −2.5, L 1.8, V −8.9 mm from bregma) using a microinjection pump (CMA/100, Carnegie Medicine, Stockholm, Sweden). After a postoperative period of 6 days or longer, apomorphine hydrochloride hemihydrate (hereinafter apomorphine, 0.1 mg/kg; Sigma-Aldrich, St. Louis, Mo., USA) was subcutaneously administered, and only the rats that showed contralateral rotational behaviors were used for the subsequent experiment.

The contralateral rotational behavior was confirmed and the number of rotations of the contralateral rotational behavior was counted in a bucket (height 28 cm, inner diameter 21 cm) with floor beddings. The subcutaneous administration or oral administration in the test was performed after about 1 hr of acclimation after placing the rats in the bucket. The number of rotations was counted using a counting instrument (own making) and a counter (Gotemba Seisakusho, Shizuoka) with a 180-degree rotation as one count.

After the lapse of 6 days or longer from the confirmation of contralateral rotational behavior, apomorphine (0.1 mg/kg) was subcutaneously administered again. Rats showing 500-1100 counts of rotation number during the first 120 min after administration were selected and grouped to make the average total count number almost equal.

After a drug withdrawal period of 6 days or longer after the grouping, the effect of the test compound on the L-DOPA induced rotational behavior was examined in each group of the rats. L-DOPA and a test compound (combined administration group), or L-DOPA and water for injection containing 0.5 weight/volume % methylcellulose (0.5% MC solution) (single administration group) were each administered orally, and the total number of rotations in 3 hr was counted. The number of rotations of each group was expressed as mean±standard deviation of total count number shown by individual rats for 3 hrs. L-DOPA was used as a mixed agent with benserazide (both produced by Kyowa Hakko Kogyo Co., Ltd., administration ratio 4:1). L-DOPA and test compound were each suspended in 0.5% MC solution. L-DOPA, 0.5% MC solution and test compound were orally administered at a dose of 0.25 mL/kg.

The results are shown in Table 2 and Table 3. In each Table, p value shows a significant difference from the L-DOPA mg/kg)+0.5% MC solution administration group.

TABLE 2

| administration group (sample size) | number of rotations |
|---|---|
| L-DOPA (10 mg/kg) + 0.5% MC solution (6) | 534.3 ± 123.4 |
| L-DOPA (10 mg/kg) + compound 1 (30 mg/kg) (5) | 1732.2 ± 305.2* |
| L-DOPA (20 mg/kg) + 0.5% MC solution (5) | 1315.2 ± 268.2* |

*p < 0.05 (Student's t-test)

TABLE 3

| administration group (sample size) | number of rotations |
|---|---|
| L-DOPA (10 mg/kg) + 0.5% MC solution (8) | 367.3 ± 140.6 |
| L-DOPA (10 mg/kg) + compound 2 (1 mg/kg) (8) | 1543.5 ± 263.2* |
| L-DOPA (20 mg/kg) + 0.5% MC solution (8) | 1641.5 ± 320.4** |

*p < 0.05,
**p < 0.01 (Student's t-test)

Results:

From the above-mentioned results, the following was clarified. Compound 1 and compound 2 significantly enhanced L-DOPA induced rotational behavior, namely antiparkinsonian activity in the Parkinson's disease model rats. The antiparkinsonian activity obtained by the administration of L-DOPA 10 mg/kg and compound 1 or compound 2 combined was of the same level as that obtained by the single administration of L-DOPA 20 mg/kg.

To be specific, it was clarified that by administrating triazolopyrimidine derivative having an adenosine $A_{2A}$ receptor antagonistic action, the dose of L-DOPA that causes motor complications in the L-DOPA treatment of Parkinson's disease can be reduced. By reducing the dose of L-DOPA that causes motor complications, it is suggested that the induction of motor complications can be delayed or suppressed.

Test Example 2

Effect on the Involuntary Movement (e.g., Dyskinesia Etc.) Model Rats

It is known that abnormal involuntary movements (AIMS) are developed by repeated administration of L-DOPA to the Parkinson's disease model rat prepared by the method described in Test Example 1, and the treated rat is used as a model of an involuntary movement such as dyskinesia, or the like. AIMs are classified into 4 kinds: (1) axial AIMs: deflection or torsion of head, neck, and trunk towards the contralateral side of lesioned side of the brain, (2) limb AIMs: movements of mainly forelimb on the contralateral side of the lesioned side of the brain (bending or extension in the perpendicular direction or movements in the horizontal•back and forth directions, opening and closure of the digits etc.); (3) orolingual AIMs: jaw movements, facial distortion, tongue protrusion (accompanying behavior of biting hair, skin of forelimb on the contralateral side of the lesioned side); and (4) locomotive AIMs: contralateral rotational behavior. Of these, locomotive AIMs are induced by dopamine agonists such as bromocriptine causing less dyskinesia, and are not suppressed by a drug having an antidyskinesia activity such as amantadine. From these, locomotive AIMs have been reported to reflect normal movements improved by an antiparkinsonian effect (Neurobiology of Disease, 2002, vol. 10, p. 165-86; European Journal of Neuroscience, 2002, vol. 15, p. 120-132).

Observation and Judgment of AIMs:

The rats were placed in transparent acrylic cages, and AIMs of each rat were observed for 1 min in every 10 min after drug administration and for a total of 3 hrs per day. The frequency of the above-mentioned four kinds of AIMs were scored in 0 to 4 points (0 point: no symptom, 1 point: appearance in less than 50% of observation time, 2 points: appearance in 50% or more of observation time, 3 points: symptom is maintained but prevented by strong sensory stimuli, 4 points: symptom is maintained and is not prevented by strong sensory stimuli). As for axial AIMs and limb AIMs, the amplitude thereof was scored in 1 to 4 points (axial AIMs; 1 point: deflection of head and neck is less than 30 degrees, 2 points: deflection of head and neck is not less than 30 degrees and less than 60 degrees, 3 points: deflection and torsion of head, neck and upper trunk is not less than 60 degrees and less than 90 degrees, 4 points: deflection and torsion of head, neck and trunk is 90 degrees or more and balance is lost, limb AIMs; 1 point: tiny oscillatory movements of limb and distal forelimb, 2 points: low amplitude but visible translocation of both distal and proximal limbs, 3 points: translocation of the whole limb with visible contraction of shoulder muscles, 4 points: strong movements of limb and shoulder at maximul amplitude).

Test Method:

SD male rats (6-week-old, CHARLES RIVER LABORATORIES JAPAN, INC.) were used for the test. Parkinson's disease model rats were prepared according to the method described in Test Example 1. After a postoperative period of 6 days or longer, L-DOPA (20 mg/kg/day) was repetitively and orally administered once or twice per day to give a model rat of involuntary movement such as dyskinesia, or the like.

AIMs were observed at day 12-14 from the start of repeated administration of L-DOPA, and the rats were grouped to make the average total score almost equal. The rats almost free of AIMs after the lapse of 1 week or longer from repetitive administration of L-DOPA were removed. As the group constitution, an L-DOPA 20 mg/kg and 0.5% MC solution administration group (single administration group) and an L-DOPA 10 mg/kg and test compound administration group (combined administration group) were used. The test compound was used in the same dose as in Test Example 1, whereby the conditions under which both the single administration group and the combined administration group show the same level of antiparkinsonian activity were set.

After grouping, multiple doses of L-DOPA 20 mg/kg and 0.5% MC solution, and L-DOPA 10 mg/kg and test compound were orally administered, respectively. At day 1-3 and 8-10 of the administration, AIMs were observed for 3 days and the effect of the test compound was examined, respectively. After the completion of administration, a 3-day drug withdrawal period was taken, and then L-DOPA (20 mg/kg) was administered. The AIMs score at this time was taken as the post value. The AIMs score of each group was expressed as mean±standard deviation of total AIMs score observed in individual rats for one day.

L-DOPA was used as a mixed agent with benserazide (both produced by Kyowa Hakko Kogyo Co., Ltd., administration ratio 4:1). L-DOPA and test compound were each suspended in 0.5% MC solution. L-DOPA, 0.5% MC solution and test compound were orally administered at a dose of 0.25 mL/kg.

The results are shown in Table 4 and Table 5. In each Table, p value shows a significant difference from the L-DOPA (20 mg/kg)+0.5% MC solution administration group.

TABLE 4

| | AIMs score | | | | | |
| --- | --- | --- | --- | --- | --- | --- |
| | axial, limb, orolingual | | | locomotive | | |
| administration group (sample size) | day 1-3 | day 8-10 | post value | day 1-3 | day 8-10 | post value |
| L-DOPA (20 mg/kg) + 0.5% MC solution (6) | 272.9 ± 25.9 | 291.7 ± 16.7 | 129.3 ± 14.3 | 16.0 ± 2.1 | 16.1 ± 2.1 | 16.3 ± 2.8 |
| L-DOPA (10 mg/kg) + compound 1 (30 mg/kg) (7) | 78.3 ± 17.2*** | 105.0 ± 24.1*** | 106.9 ± 14.0 | 16.3 ± 3.5 | 16.4 ± 3.9 | 17.1 ± 3.1 |

***$p < 0.001$ (Student's t-test)

TABLE 5

| administration group (sample size) | AIMs score | | | | | |
|---|---|---|---|---|---|---|
| | axial, limb, orolingual | | | locomotive | | |
| | day 1-3 | day 8-10 | post value | day 1-3 | day 8-10 | post value |
| L-DOPA (20 mg/kg) + 0.5% MC solution (6) | 271.9 ± 12.6 | 232.4 ± 26.2 | 139.1 ± 12.6 | 12.4 ± 2.6 | 13.6 ± 1.7 | 15.0 ± 1.4 |
| L-DOPA (10 mg/kg) + compound 2 (1 mg/kg) (7) | 146.4 ± 13.3*** | 117.5 ± 15.5** | 159.8 ± 24.7 | 14.8 ± 1.7 | 14.4 ± 1.7 | 13.1 ± 1.7 |

**p < 0.01,
***p < 0.001 (Student's t-test)

Results:

From the above-mentioned results, the following was clarified. The combined administration of L-DOPA 10 mg/kg and compound 1 or compound 2 resulted in significant suppression of the onset of dyskinesia as compared to single administration of L-DOPA 20 mg/kg, while maintaining the antiparkinsonian activity of the same level as that obtained by single administration of L-DOPA 20 mg/kg.

To be specific, it was clarified that the administration of a triazolopyrimidine derivative having an adenosine $A_{2A}$ receptor antagonistic action could reduce the dose of L-DOPA that causes motor complications in the treatment of Parkinson's disease with L-DOPA, and the induction of dyskinesia, which is one of the motor complications, can be delayed or suppressed.

From the results of the Test Examples above, it is suggested that a triazolopyrimidine derivative having an adenosine $A_{2A}$ receptor antagonistic action or a pharmaceutically acceptable salt thereof is effective for preventing and/or treating involuntary movements (for example, tremor, dyskinesia, chorea, ballism, dystonia, ataxia, athetosis, tic, myoclonus etc.) and a combination of these symptoms, and movement disorders characterized by one or more symptoms therefrom [for example, motor complications (e.g., dyskinesia, on-off fluctuation, wearing-off phenomenon etc.) in the treatment of Parkinson's disease with L-DOPA and/or a dopamine agonist etc., Huntington's disease, essential tremor, tardive dyskinesia, tardive dystonia, Tourette syndrome, progressive supranuclear palsy, spasmodic torticollis etc.].

A triazolopyrimidine derivative having an adenosine $A_{2A}$ receptor antagonistic action or a pharmaceutically acceptable salt thereof can be used as it is or in various formulation forms. The pharmaceutical composition of the present invention can be produced by uniformly mixing, as an active ingredient, an effective amount of a triazolopyrimidine derivative having an adenosine $A_{2A}$ receptor antagonistic action or a pharmaceutically acceptable salt thereof with a pharmaceutically acceptable carrier. Such pharmaceutical composition is desirably in a unit dosage form suitable for, for example, oral or parenteral (including subcutaneous, intravenous and intramuscular) administration, or the like.

For the preparation of a composition in an oral dosage form, some useful pharmaceutically acceptable carrier can be used. For example, an oral liquid preparation such as suspension and syrup can be produced using water, saccharides such as sucrose, sorbitol or fructose, glycols such as polyethylene glycol or propylene glycol, oils such as sesame oil, olive oil, or soybean oil, preservatives such as p-hydroxybenzoates, flavors such as strawberry flavor, peppermint, or the like. Powder, pill, capsule and tablet can be produced using excipients such as lactose, glucose, sucrose, or mannitol, disintegrants such as starch or sodium alginate, lubricants such as magnesium stearate or talc, binders such as polyvinylalcohol, hydroxypropylcellulose or gelatin, surfactants such as fatty acid ester, plasticizer such as glycerol, and the like. Since it is easy to administer, tablet and capsule are most useful unit agents for oral administration. For production of tablet and capsule, a solid pharmaceutical carrier is used.

In addition, injection can be prepared using a carrier comprising distilled water, salt solution, glucose solution or a mixture of salt water and glucose solution, or the like. In this case, it is prepared as a solution, suspension or dispersion solution using a suitable auxiliary agent according to a conventional method.

A triazolopyrimidine derivative having an adenosine $A_{2A}$ receptor antagonistic action or a pharmaceutically acceptable salt thereof can be administered orally in the above-mentioned formulation form or parenterally as an injection, or the like, where its effective dose and administration frequency vary depending on the dosage form, age, body weight, symptom, and the like of patients. It is suitably administered at a dose of 1-100 mg/60 kg/day, preferably 1-20 mg/60 kg/day once or several times a day.

In addition, a triazolopyrimidine derivative having an adenosine $A_{2A}$ receptor antagonistic action or a pharmaceutically acceptable salt thereof can also be used in combination with one or more pharmaceutical agents selected from, for example, L-DOPA, dopamine agonist, MAO-B inhibitor, COMT inhibitor, and the like.

The embodiments of the present invention are explained in the following by referring to Examples.

Example 1

Tablet

Tablets having the following composition are prepared by a conventional method.

Compound 1 (40 g), lactose (286.8 g) and potato starch (60 g) are mixed and 10% aqueous hydroxypropylcellulose solution (120 g) is added thereto. This mixture is kneaded by a conventional method, and then granulated, dried and sized to give granules for tabletting. Magnesium stearate (1.2 g) is added thereto and mixed and the mixture is tableted using a tabletting machine (manufactured by Kikusui Ltd. RT-15 type) having a punch with a diameter of 8 mm to give tablets (containing 20 mg of active ingredient per tablet).

Example 2

Capsule

Capsules having the following composition are prepared by a conventional method.

Compound 2 (200 g), Avicel (995 g) and magnesium stearate (5 g) are mixed by a conventional method. The mixture is filled in a hard capsule No. 4 (120 mg per 1 capsule) by a capsule filling machine (manufactured by Zanasi Co., LZ-64 type) to give capsule (containing 20 mg of active ingredient pet capsule).

| formulation | |
|---|---|
| compound 1 | 20 mg |
| lactose | 143.4 mg |
| potato starch | 30 mg |
| hydroxypropylcellulose | 6 mg |
| magnesium stearate | 0.6 mg |
| | 200 mg |

| formulation | |
|---|---|
| compound 2 | 20 mg |
| Avicel | 99.5 mg |
| magnesium stearate | 0.5 mg |
| | 120 mg |

Example 3

Injection

Injection having the following composition is prepared by a conventional method.

Compound 1 (1 g) is dissolved in purified soybean oil (100 g), and purified egg-yolk lecithin (12 g) and glycerol for injection (25 g) are added. This mixture is adjusted to 1000 mL with distilled water for injection and kneaded and emulsified by a conventional method. The obtained dispersion is sterilized by filtration using a 0.2 μm disposable membrane filter, and aseptically filled in a glass vial by 2 mL to give an injection (containing 2 mg of active ingredient per vial).

| formulation | |
|---|---|
| compound 1 | 2 mg |
| purified soybean oil | 200 mg |
| purified egg-yolk lecithin | 24 mg |
| glycerol for injection | 50 mg |
| distilled water for injection | 1.72 mL |
| | 2.00 mL |

INDUSTRIAL APPLICABILITY

According to the present invention, for example, an agent for preventing and/or treating movement disorder comprising, as an active ingredient, a triazolopyrimidine derivative having an adenosine $A_{2A}$ receptor antagonistic action or a pharmaceutically acceptable salt thereof, and the like can be provided.

The invention claimed is:

1. A method of treating a motor complication in the treatment of Parkinson's disease, which comprises administering an effective amount of a compound represented by the formula (2)

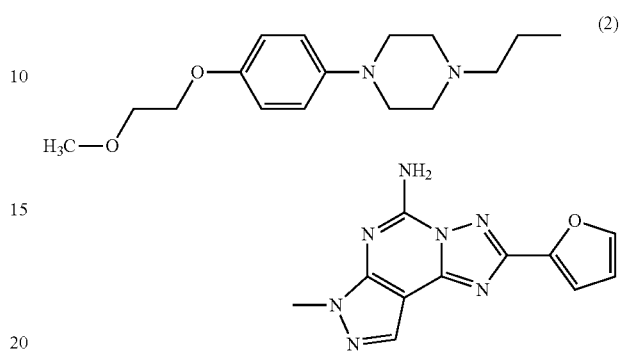

or a pharmaceutically acceptable salt thereof to a patient with a motor complication in the treatment of Parkinson's disease, thereby treating the motor complication in the patient.

2. The method according to claim 1, wherein the motor complication is a motor complication in the treatment of Parkinson's disease with L-DOPA and/or a dopamine agonist.

3. The method according to claim 1, wherein the motor complication is dyskinesia in the treatment of Parkinson's disease.

4. The method according to claim 1, wherein the motor complication in the treatment of Parkinson's disease is dyskinesia in the treatment of Parkinson's disease with L-DOPA and/or a dopamine agonist.

5. A method of reducing the dose of L-DOPA in the treatment of Parkinson's disease with L-DOPA alone or in combination with a dopamine agonist, which comprises administering an effective amount of a compound represented by the formula (2)

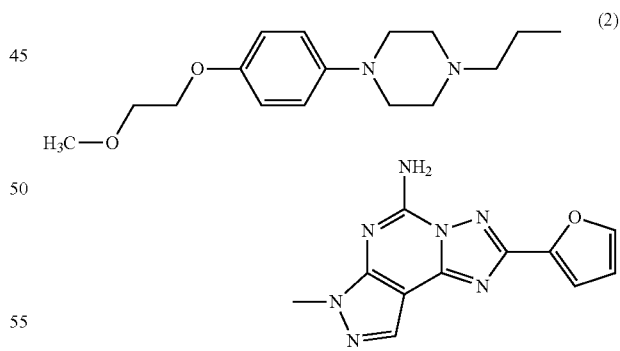

or a pharmaceutically acceptable salt thereof to a patient with Parkinson's disease being treated with a dose of L-DOPA alone or in combination with a dopamine agonist, thereby allowing the dose of L-DOPA administered to the patient to be reduced as compared to the dose of L-DOPA administered to the patient prior to the administration of the compound represented by the formula (2).

* * * * *

UNITED STATES PATENT AND TRADEMARK OFFICE
CERTIFICATE OF CORRECTION

| | | |
|---|---|---|
| PATENT NO. | : 7,851,478 B2 | Page 1 of 1 |
| APPLICATION NO. | : 11/916783 | |
| DATED | : December 14, 2010 | |
| INVENTOR(S) | : Kadowaki et al. | |

It is certified that error appears in the above-identified patent and that said Letters Patent is hereby corrected as shown below:

IN THE CLAIMS:

Claim 1, at column 20, the chemical formula at lines 6-22, should read:

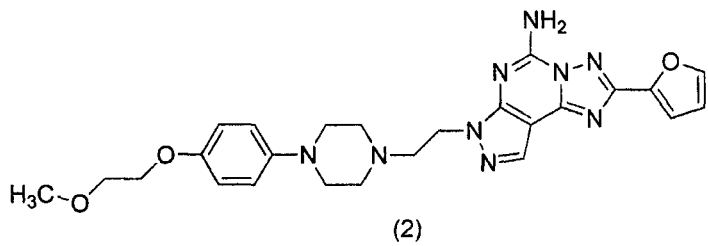

(2)

Claim 5, at column 20, the chemical formula at lines 42-57, should read:

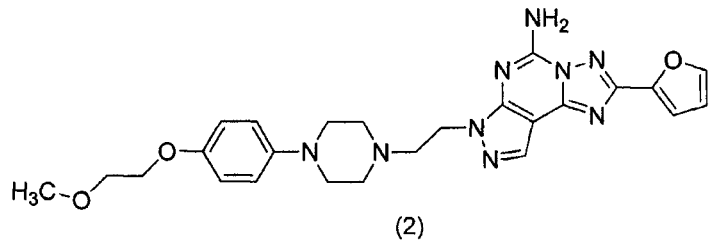

(2)

Signed and Sealed this
Twenty-fourth Day of May, 2011

David J. Kappos
*Director of the United States Patent and Trademark Office*